United States Patent [19]
Thompson

[11] Patent Number: 5,360,437
[45] Date of Patent: Nov. 1, 1994

[54] IMPLANTABLE MEDICAL DEVICE WITH FLEXIBLE HARDWARE PLATFORM

[75] Inventor: David L. Thompson, Fridley, Minn.

[73] Assignee: Medtronic, Inc., Minneapolis, Minn.

[21] Appl. No.: 149,161

[22] Filed: Nov. 8, 1993

Related U.S. Application Data

[63] Continuation of Ser. No. 785,841, Oct. 31, 1991, abandoned.

[51] Int. Cl.$^5$ .............................. A61N 1/362
[52] U.S. Cl. .......................... 607/30; 607/60
[58] Field of Search ............... 607/30, 31, 32, 60

[56] References Cited
U.S. PATENT DOCUMENTS

| | | | |
|---|---|---|---|
| 4,147,165 | 4/1979 | Tauschinski | 128/214.4 |
| 4,166,469 | 9/1979 | Littleford | 128/784 |
| 4,243,050 | 1/1981 | Littleford | 128/784 |
| 4,306,562 | 12/1981 | Osborne | 128/348 |
| 4,345,606 | 8/1982 | Littleford | 128/784 |
| 4,411,654 | 10/1983 | Boarini et al. | 604/165 |
| 4,459,989 | 7/1984 | Borkan | 607/60 |
| 4,581,025 | 4/1986 | Timmermans | 604/264 |
| 4,596,559 | 6/1986 | Fleischhacker | 604/170 |
| 4,687,469 | 8/1987 | Osypka | 604/161 |
| 4,712,179 | 12/1987 | Heimer | 128/903 |
| 4,809,697 | 3/1989 | Causey, III et al. | 128/903 |
| 5,029,128 | 7/1991 | Toda | 365/145 |
| 5,080,096 | 1/1992 | Hooper et al. | 128/419 P |
| 5,081,987 | 1/1992 | Nigam | 607/30 |
| 5,098,392 | 3/1992 | Fleischhacker | 604/165 |
| 5,127,404 | 7/1992 | Wyborny et al. | 128/903 |

OTHER PUBLICATIONS
One page depicting competitors' lead introducers.

*Primary Examiner*—George Manuel
*Attorney, Agent, or Firm*—Reed A. Duthler; Harold R. Patton

[57] ABSTRACT

A medical device providing a flexible hardware platform to support alternative therapeutic functions is disclosed. In one embodiment, a microprocessor-based pacemaker incorporates a non-volatile ferroelectric random access read/write memory (FRAM) for storing microprocessor instructions defining a pacing algorithm. Information in the FRAM may be re-written after implant of the pacemaker in a patient via the pacemaker's telemetry link, so that the pacemaker's pacing function may be upgraded or replaced without explant of the pacemaker. The non-volatility of the FRAM ensures that the pacing function is not erased if power to the pacemaker is momentarily interrupted. The flexible hardware platform allows a single type of pacemaker to be implanted in patients with varying cardiac conditions and pacing requirements, thus reducing the inventory requirements of hospitals. The pacing function in pacemakers for patients with progressive or otherwise changing medical conditions can be modified in accordance with the patients' changing needs without invasive procedures. Rewriting of the pacing function is carried out separately from conventional modification of mode selection and parameter value programming. Other information, including parameter data, implant data, patient medical data, and device identification data may also be stored in the FRAM.

9 Claims, 2 Drawing Sheets

IMPLANTABLE MEDICAL DEVICE WITH FLEXIBLE HARDWARE PLATFORM

"This is a continuation of copending application(s) Ser. No. 07/785,841 filed on Oct. 31, 1991 now abandoned".

FIELD OF THE INVENTION

This invention relates generally to the field of implantable medical devices, and more particularly relates to microprocessor-based or software-controlled implantable medical devices.

BACKGROUND OF THE INVENTION

A wide variety of implantable medical devices are known and commercially available, including implantable cardiac pacemakers, cardioverters, and defibrillators, implantable neural stimulators, and implantable drug-administering devices. In the case of cardiac pacemakers, a variety of operational modes, or "pacing functions" have been defined. Pacemakers are generally characterized by which chambers of the heart they are capable of sensing, the chambers to which they deliver pacing stimuli, and their responses, if any, to sensed intrinsic cardiac activity. Some pacing functions specify that delivery of pacing stimuli is at fixed, regular intervals without regard to naturally occurring cardiac activity. Other pacing functions, however, specify that delivery of pacing stimuli is to be inhibited and/or triggered based upon sensed electrical cardiac activity in one or both of the chambers of the patient's heart. A so-called "VVI" pacemaker, for example, senses electrical cardiac activity in the ventricle of the patient's heart, and delivers pacing stimuli to the ventricle only in the absence of electrical signals indicative of natural ventricular contractions. A "DDD" pacemaker, on the other hand, senses electrical signals in both the atrium and ventricle of the heart, and delivers pacing stimuli only in the absence of appropriately timed natural atrial contractions, and ventricular pacing stimuli only in the absence of appropriately timed natural ventricular contractions. The delivery of each pacing stimuli by a DDD pacemaker is synchronized as much as possible with the patient's natural cardiac activity, as evidenced by prior sensed cardiac events.

Pacemakers are also known which respond to other types of physiologically-based signals, such as signals from sensors for measuring the pressure inside the patient's heart or for measuring the level of the patient's physical activity. In this way, the pacemaker's rate of delivery of pacing stimuli may be increased or decreased in correspondence with the patient's level of physical activity and demand for cardiac output.

The use of a pacemaker with a certain modality in a given patient is determined by the physician based upon several factors, including the nature and extent of patient's particular cardiac condition, and the patient's age and lifestyle. In addition, for a given pacing function, various operational parameters, such as pacing rate, A-V delay, pacing amplitude, sense amplifier sensitivity, and so on, must also be determined for each patient individually. Moreover, because a patient's cardiac condition is typically not static, (i.e. the patient can either show improvement or degradation in his condition), the indications for a particular pacing function and for particular parameter settings are subject to change over the years that the pacemaker may be implanted. In addition, a patient's cardiac condition at the time of implant may be difficult or impossible to diagnose, making it difficult for the implanting physician to determine what modality of pacemaker is indicated or what parameter values should be set.

The need to customize the pacing mode and pacing parameters for each patient at the time of implant, and the possibility that the mode and parameters might need to be altered over time has led to the development of various programmable pacemakers, in which the pacing mode and pacing parameters may be set and/or modified even after the pacemaker has been implanted in the patient. Today, nearly all pacemakers have at least some degree of post-implant programmable capability. Very sophisticated pacemakers may be programmed to operate in one of many different modes with a wide range of selectable parameter settings within each mode. Such programmable flexibility in implanted medical devices has proven to be very desirable, as evidenced by the widespread commercial success of these devices.

One disadvantage of pacemakers which are capable of being programmed into a variety of different pacing modes, with each mode having a wide range of programmable parameter selections, is that such pacemakers are typically larger, heavier, and more expensive than pacemakers operable in only one or a few modes, with relatively fewer programmable parameter options. Research and development costs, testing costs, manufacturing costs, battery consumption, and failure rates are all typically higher with programmable multi-mode devices than with simpler, single-mode devices. For these reasons, programmable multi-mode pacemakers have not entirely displaced single-mode devices in the market place. In addition, patients with readily diagnosed conditions may require, at least at the time of implant, only a simple, single-mode device, making the use of an sophisticated and expensive multi-mode device unnecessary and undesirable. However, these patients' conditions may nonetheless change over time, or new pacemaker features may be developed which are particularly well-suited to these patients. If a patient's pacemaker is not sufficiently programmable, making newly indicated or newly developed features available to that patient involves the removal of the old pacemaker, and the purchase and implantation of a new pacemaker. Replacement of a patient's pacemaker may also be required if his condition was initially mis-diagnosed.

Since the particular type of pacemaker that is required by a patient cannot be determined until that patient's cardiac condition is completely diagnosed, hospitals must maintain a large inventory of pacemakers of all modes, so that when the patients' conditions are diagnosed, the appropriate pacemakers are readily available. As pacemakers typically cost three to five thousand dollars, maintaining large inventories of these devices tends to increase hospital costs.

In most commercially available programmable medical devices, the selection for a programmable operational mode or selected values for operational parameters is stored in conventional random-access memory (RAM) within the device. One drawback of storing modes and parameter values in RAM is that conventional RAM devices are volatile memory devices; that is, information stored in a RAM is lost when power to the RAM is interrupted. Thus, most RAM-based programmable devices are provided with a set of "default" modes and parameters which define the operation of the device when it is first powered-up, or when power to the device is momentarily interrupted.

Although the selection of a particular operational mode is typically stored in RAM, the actual control instructions corresponding to the pacing function of each of the selectable modes in the pacemaker are usually stored in read-only memory (ROM) within the pacemaker. The selection stored in RAM, therefore, merely selects one of the pacing function definitions stored in ROM to be used for operational control of the pacemaker. Storing the pacing function in RAM is not generally considered acceptable, since a momentary interruption in power would completely disable the pacemaker, its instructions for executing a particular pacing mode having been lost due to the volatility of RAM. One disadvantage of storing the pacing function in ROM, however, is that the pacing function cannot be changed by means of external programming. If the pacing function is stored in ROM, only the selection of a particular pacing function, not the definition of that pacing function, can be changed via external programming.

In view of the factors mentioned in the foregoing discussion, the inventor has determined that it would be desirable to provide a pacemaker in which the pacing algorithm can be re-defined after implant by means of external, non-invasive programming, as is commonly used for selecting pacing modes and operational parameters.

It would therefore be desirable for a pacemaker to incorporate a memory device for storing the pacing function definition which combines the re-programmability of RAM with the non-volatility of ROM, so that the pacing function definition would not be lost in a momentary interruption of power to the device. If the memory were re-programmable like RAM, newly-developed pacing features could be implemented in pacemakers which were implanted before development of those features. Patients whose cardiac condition has changed since the time of implant of their pacemakers could have their pacing functions modified to accommodate their changed conditions.

SUMMARY OF THE INVENTION

According to the present invention, a pacemaker is provided in which operation is microprocessor-controlled, and in which the "program" which defines the pacing algorithm performed under microprocessor control is stored in a non-volatile RAM. The non-volatility of the RAM allows the selected mode of the pacemaker to be preserved even when power to the pacemaker is interrupted.

The disclosed pacemaker provides a general-purpose hardware "platform" which is generally compatible with a variety of different pacing modes; that is, the pacemaker hardware could support anything from simple single-chamber, asynchronous pacing to complex dual-chamber, synchronous, rate-responsive pacing with extensive monitoring and diagnostic features. The pacing function executed by the pacemaker hardware would be defined by software stored in the non-volatile RAM. When new pacing functions or enhancements to existing pacing functions are developed, these functions could be incorporated into the implanted device via external programming, not requiring replacement of the pacemaker hardware. Similarly, if a patient's cardiac condition changed following implantation of the pacemaker, the pacemaker's pacing function could be redefined accordingly, also without requiring replacement of the pacemaker.

BRIEF DESCRIPTION OF THE DRAWINGS

The foregoing and other features of the present invention will be best appreciated with reference to the detailed description of a specific embodiment of the invention, which follows, when read in conjunction with accompanying drawings, wherein.

DETAILED DESCRIPTION OF SPECIFIC EMBODIMENTS OF THE INVENTION

Figure 1:
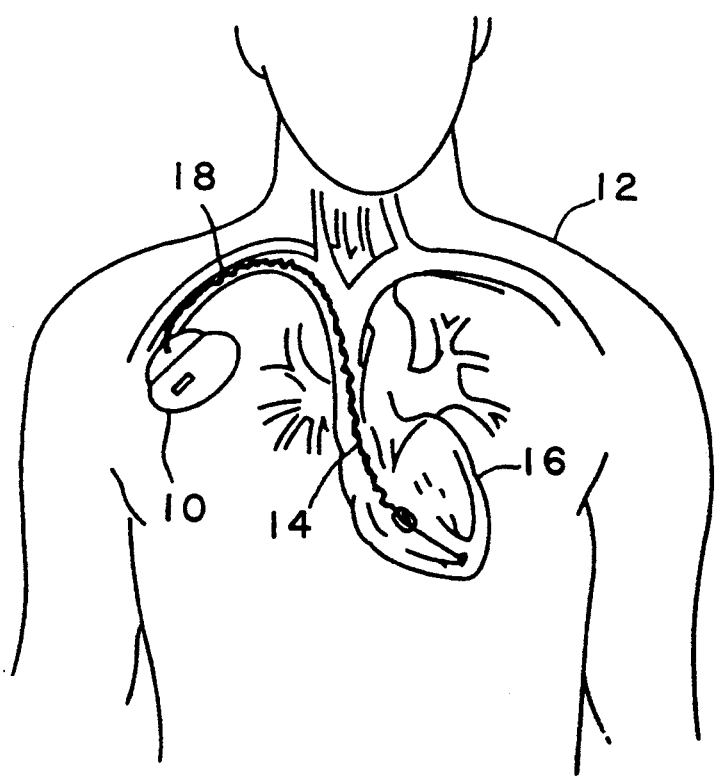
FIG. 1 is a diagram showing the placement in a patient of a pacemaker in accordance with one embodiment of the present invention.

FIG. 1 shows generally how a pacemaker 10 in accordance with the present invention may be implanted in a patient 12. A pacemaker lead 14 is electrically coupled to pacemaker 10 and extends into the patient's heart 16 via a vein 18. The distal end of lead 14 includes one or more exposed conductive electrodes for receiving electrical cardiac signals and for delivering electrical pacing stimuli to the patient's heart 16.

Figure 2:
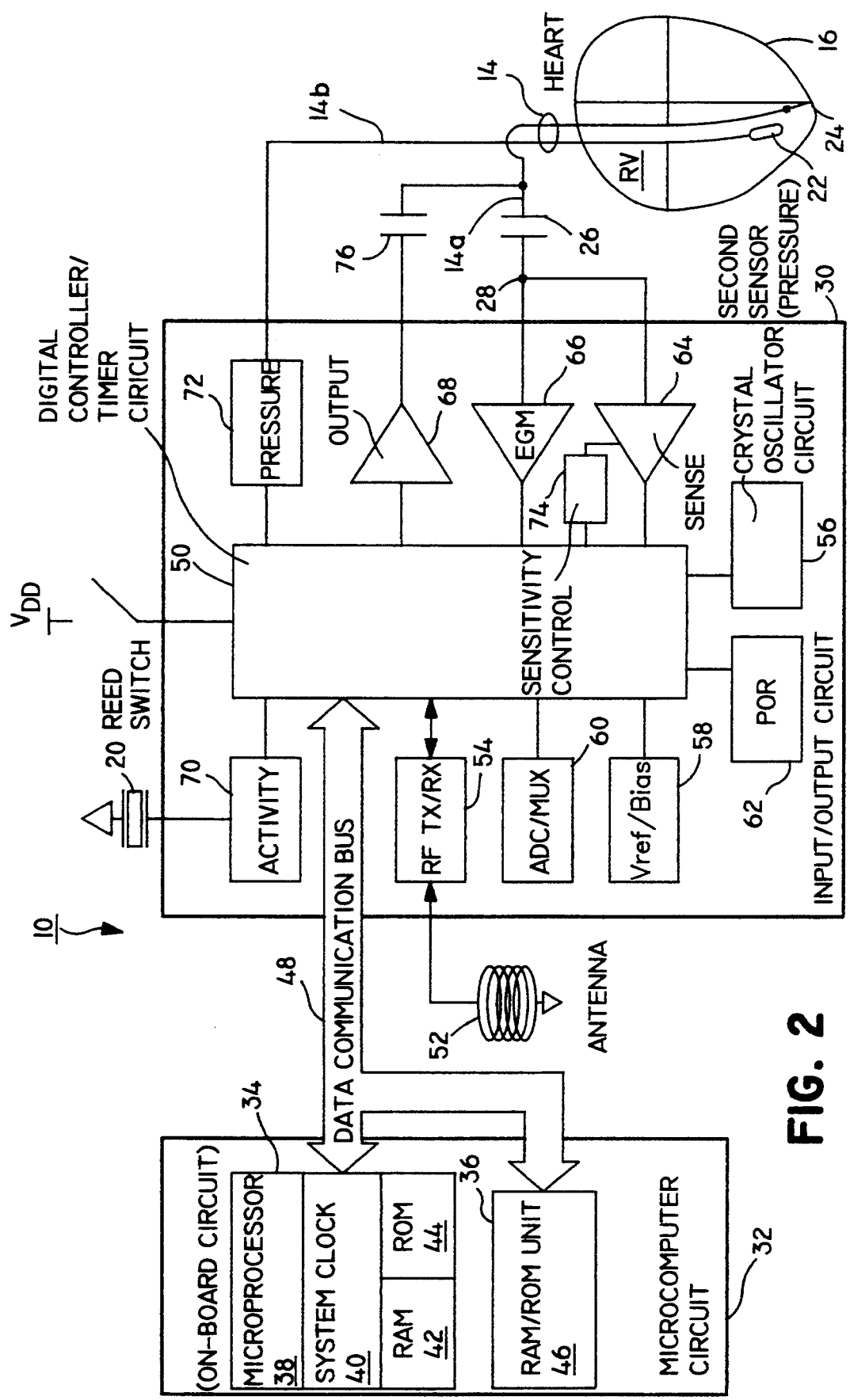
FIG. 2 is a block diagram of the circuitry of the pacemaker of FIG. 1.

Turning to FIG. 2, a block diagram of pacemaker 10 from FIG. 1 is shown. Although the present invention is described in conjunction with a pacemaker 10 having a microprocessor-based architecture, it will be understood that it could be implemented in a digital logic based, custom integrated circuit architecture, if desired. It will also be understood that the present invention may be utilized in conjunction with other implantable medical devices, such as cardioverters, defibrillators, neural stimulators, and the like.

In the embodiment shown in FIG. 1, pacemaker 10 includes an activity sensor 20, which may be, for example, a piezoelectric element bonded to the inside of the pacemaker's housing. Sensor 20 provides a sensor output which varies as a function of a measured parameter that relates to the metabolic requirements of patient 12. In addition, pacemaker 10 may include a pressure sensor 22, which may be similarly used to ascertain the metabolic requirements and/or cardiac output of patient 12. Pressure sensor 22 may be a piezoelectric element such as is disclosed in U.S. Pat. No. 4,407,296 to Anderson, entitled "Integral Hermetic Implantable Pressure Transducer", or U.S. Pat. No. 4,485,813 to Anderson et al., entitled "Implantable Dynamic Pressure Transducer System", each assigned to the assignee of the present invention and incorporated herein by reference.

Pacemaker 10 is schematically shown in FIG. 2 to be electrically coupled via a pacing lead 14 to a patient's heart 16. Lead 14 includes an intracardiac electrode 24 and pressure sensor 22 located near its distal end and positioned within the right ventricular (RV) chamber of heart 16. Lead 14 can carry either unipolar or bipolar electrodes as is well known in the art. In the presently disclosed embodiment, lead 14 which couples pacemaker 10 to the ventricular endocardium can comprise a steroid-tipped, unipolar lead with an integral pressure transducer of the type described in the aforementioned references. Electrode 24 is coupled via suitable lead conductor 14a through input capacitor 26 to node 28 and to input terminals of an input/output circuit 30. Output from first sensor 20 is coupled to input/output circuit 30. Output from pressure sensor 22 is also coupled to input/output circuit 30 via suitable lead conductor 14b.

Input/output circuit 30 contains the operating input and output analog circuits for digital controlling and timing circuits necessary for the detection of electrical signals derived from heart 16, such as the cardiac electrogram (EGM), output from first sensor 20, and the output from pressure sensor 22, as well as for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. Off-board circuit 36 includes an off-board RAM/ROM unit 46 which shall be hereinafter described in greater detail. Microcomputer circuit 32 is coupled by data communication bus 48 to a digital controller/timer circuit 50. Microcomputer circuit 32 may be fabricated of custom integrated circuit devices augmented by standard RAM/ROM components.

It will be understood that the electrical components represented in FIG. 2 are powered by an appropriate implantable battery power source, not shown, in accordance with common practice in the art.

An antenna 52 is connected to input/output circuit 30 for purposes of uplink/downlink telemetry through RF transmitter/receiver (RF TX/RX) unit 54. Telemetering both analog and digital data between antenna 52 and an external device, such as an external programmer (not shown), is accomplished in the presently disclosed embodiment by means of all data first being digitally encoded and then pulse-position modulated on a damped RF carrier, as substantially described in co-pending U.S. patent application Ser. No. 468,407, filed on Jan. 22, 1990, entitled "Improved Telemetry Format", which is assigned to the assignee of the present invention and which is incorporated herein by reference.

A crystal oscillator circuit 56, typically a 32,768-Hz crystal-controlled oscillator, provides main timing clock signals to digital controller/timer circuit 50. A Vref/Bias circuit 58 generates stable voltage reference and bias currents for the analog circuits of input/output circuit 30. An analog-to-digital converter/multiplexor (ADC/MUX) unit 60 digitizes analog signals and voltages to provide telemetry and battery end-of-life (EOL) replacement function. A power-on-reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input/output circuit 30.

Digital controller/timer circuit 50 is coupled to a sense amplifier 64 and an electrogram amplifier 66 for receiving amplified and processed signals picked up from electrode 24 through lead conductor 14a and capacitor 26 representative of the electrical activity of the patient's heart 16. Sense amplifier 64 produces a sensed event signal for resetting the escape interval timer within circuit 50. The electrogram signal developed by EGM amplifier 66 is used in those occasions when the implanted device is being interrogated by an external programmer, not shown, in order to transmit by uplink telemetry a representation of the analog electrogram of the patient's electrical heart activity as described in U.S. Pat. No. 4,556,063, issued to Thompson et al., assigned to the assignee of the present invention and incorporated herein by reference. An output pulse generator 68 provides the pacing stimulus to the patient's heart 16 via output capacitor 76 in response to a pacing trigger signal developed by digital controller/timer circuit 50 each time the escape interval times out, or an externally transmitted pacing command has been received, or in response to other stored commands as is well known in the pacing art.

Digital controller/timer circuit 50 is coupled to an activity circuit 70 for receiving, processing, and amplifying signals received from activity sensor 20. Activity circuit 70 produces an activity signal which is representative of the patient's metabolic requirements. Similarly, digital controller/timer circuit 50 is coupled to a pressure circuit 72 for receiving, amplifying and processing sensor output from pressure sensor 22. In the presently disclosed embodiment of the invention, pressure circuit 72 produces a pressure signal which is asserted only when the sensor output from pressure sensor 22 indicates that pressure in the patient's right ventricle has exceeded a predetermined pressure threshold value. When the pressure exceeds the pressure threshold value, this is called a "true" pressure beat, and causes pressure circuit 72 to assert the pressure signal received by digital controller/timer circuit 50. Pressures which do not exceed this value are called "false" pressure beats, and do not lead to assertion of the pressure signal.

In accordance with the present invention, RAM/ROM unit 46 preferably includes a non-volatile, static random access memory device. One such device is a so-called "ferroelectric" RAM, or FRAM. FRAMs are non-volatile read/write memory devices which incorporate ferroelectric materials such as Rochelle salt, barium titinate, and lead titinate that can retain a permanent electrical field after being induced by a transient external voltage. The FMx 801, a 256×1 bit CMOS FRAM is commercially available from Ramtron Corporation, Colorado Springs, Colo. FRAMs are also commercially available from Krysalis Corporation, Albuquerque, N.M.

In pacemaker 10 of FIG. 2, RAM/ROM unit 46 which includes an FRAM for storing the sequence of instructions defining the pacing function for pacemaker 10. That is, operation of pacemaker 10 is controlled by microprocessor 38 executing instructions read on bus 48 from RAM/ROM unit 46.

Prior to implantation of pacemaker 10 in a patient, an initial pacing function is loaded into RAM/ROM unit 46. The pacing function stored in RAM/ROM unit 46 may constitute a program defining a plurality of selectable pacing modalities, as in the case of prior multi-mode pacemakers, or a program defining only a single mode of pacing, as in the case of prior single-mode pacemakers. RAM/ROM unit 46 may store, in the non-volatile FRAM, physician-selected modes and parameter values appropriate for the patient. Additionally, patient implant data, such as implant date, disease state, following center, threshold voltages, lead model, serial numbers, and the like, may be programmed into the pacemaker for subsequent readout. This data would be most useful at a center other than the implanting or initial following center. Such data, if stored in conventional RAM in the pacemaker, however, could be lost in any situation in which power to the RAM is momentarily interrupted, such as during defibrillation or electrocautery procedures, or when the pacemaker is exposed to high-level electromagnetic fields.

After implant, the pacing mode and parameter values for pacemaker 10 may be re-programmed via radio-frequency telemetry, as is well-known in the art. In addition, however, if the physician determines that a pacing mode not supported by the pacing function stored in RAM/ROM unit 46 is indicated for the patient, a special programming command may be issued to the pacemaker to over-write the pacing function stored in the FRAM of RAM/ROM unit 46 with a new pacing function.

For example, during a patient's follow-up visit to the physician, the physician may desire to temporarily program the pacemaker to operate in an asynchronous mode for the purpose of diagnosis of the patient's condition. Subsequently, the physician may program the pacemaker to a monitoring or diagnostic mode of operation, to allow detection of transient cardiac function. Later, the physician may desire to return pacemaker 10 to its previous synchronous mode of operation. If a particular pacing function loaded into the FRAM of RAM/ROM unit was behaving anomalously, the pacing function could be replaced without explant. As new pacing modalities or refinements and enhancements of existing pacing modalities are developed, these pacing modalities could be implemented in pacemaker 10 without explant by replacing the pacing function stored in RAM/ROM unit 46. The development of refinements or enhancements may be facilitated and verified by programming a limited number of patients during a research or clinical phase before programming a broad number of patients.

The non-volatility of the FRAM eliminates the potential for interruptions in the power supply from resetting or losing altogether the program function, program variables, or diagnostic stored data. These interruptions occur during defibrillation or electrocautery procedures or from high level electromagnetic interference.

From the foregoing detailed descriptions of a particular embodiment of the invention, it should be apparent that a pacemaker has been disclosed which provides a flexible hardware platform allowing non-invasive redefinition of the pacing function. Incorporation of an FRAM allows the pacing function to be re-defined while at the same time ensuring that momentary interruption of power to the pacemaker will not disable the device or modify programmed variables. While a particular embodiment of the present invention has been described herein in detail, it is to be understood that various alterations, modifications, and substitutions can be made therein without departing from the spirit and scope of the present invention, as defined in the claims, which follow. In particular, it is contemplated by the inventor that the present invention may be incorporated into various different types of implanted, microprocessor-controlled medical devices, such as implantable cardioverters, defibrillators, neural stimulators, drug-administering devices, or other implantable devices which automatically administer therapy to a patient under control of a predefined operational algorithm.

What is claimed is:

1. An implantable cardiac pacemaker, comprising:
    a pulse generator, including a microprocessor, for delivering pacing pulses to a patient's heart according to a predetermined pacing algorithm;
    non-volatile, random-access, read/write memory, for storing instructions executed by said microprocessor, said instructions defining said pacing algorithm;
    telemetry circuit means for receiving telemetry signals from a programmer external to said patient after implant of said pacemaker in said patient, said telemetry signals comprising commands and instructions for execution by said microprocessor; and
    wherein one of said commands causes said instructions stored in said random-access memory to be overwritten with said instructions in said telemetry signals, such that said predetermined pacing algorithm is modified.

2. An implantable cardiac pacemaker, comprising:
    a pulse generator, including a microprocessor, for delivering pacing pulses to a patient's heart according to a predetermined pacing algorithm;
    non-volatile, random-access, read/write memory, for storing a sequence of instructions for execution by said microprocessor, said sequence of instructions defining said pacing algorithm;
    telemetry circuit means for receiving telemetry signals from a programmer external to said pacemaker, said telemetry signals comprising commands and instructions for execution by said microprocessor; and
    wherein one of said commands causes said instructions stored in said random-access memory to be overwritten with said instructions in said telemetry signals to define a new sequence of
    instructions for execution by said microprocessor, thereby defining a new pacing algorithm.

3. A pacemaker according to claim 1 or claim 2 wherein;
    said memory further has initial operational parameters stored therein for controlling operation of said pacemaker;
    wherein said telemetry circuit means further comprises means for receiving telemetry signals which signals further comprise operational parameters for controlling operation of said pacemaker; and
    wherein one of said commands in said telemetry signals causes said initial operational parameters stored in said random-access memory to be overwritten with operational signals in said telemetry signals to modify operation of said pacemaker.

4. A pacemaker according to claim 2 wherein said telemetry circuit means comprises means for receiving telemetry signals from a programmer external to said patient after implant of said pacemaker.

5. A method of operating an implantable medical device having a non-volatile memory device therein, comprising the steps of:
    (a) providing a sequence of instructions defining an operational algorithm for said device in said non-volatile memory;
    (b) implanting said device in a patient; and
    (c) following implant, over-writing said set of instructions with an alternate set of instructions defining a new operational algorithm via non-invasive telemetry.

6. A method of operating an implantable medical device having a non-volatile memory device therein, comprising the steps of:
   (a) providing a set of data controlling operation of said device in said non-volatile memory;
   (b) implanting said device in a patient; and
   (c) following implant, over-writing said data to modify operation of said device via non-invasive telemetry.

7. A medical device, implantable in a patient, comprising:
   a non-volatile, random-access, read/write memory device, said memory device having initial instructions stored therein defining an operational algorithm for said medical device;
   a microprocessor, coupled to said memory device, said microprocessor issuing control signals in accordance with said instructions;
   therapy-delivering means for delivering a therapy to said patient under control of said control signals;
   telemetry circuit means for receiving alternate instructions transmitted from a source external to said medical device, and for providing said alternate instructions to said memory device to replace at least a portion of said initial instructions and thereby define a new operational algorithm.

8. A medical device, implantable in a patient, comprising:
   a non-volatile, random-access, read/write memory device, said memory device having initial operational parameters stored therein for controlling a operation of said medical device;
   a microprocessor, coupled to said memory device, said microprocessor issuing control signals in accordance with said operational parameters; therapy-delivering means for delivering a therapy to said patient under control of said control signals;
   telemetry circuit means for receiving alternate operational parameters transmitted from a source external to said patient after implant, and for providing said alternate operational parameters to said memory device to replace at least a portion of said initial operating parameters and thereby modify operation of said medical device.

9. A pacemaker according to claim 8 wherein said telemetry circuit means comprises means for receiving telemetry signals from a source external to said patient after implant of said pacemaker in said patient.

* * * * *